US009958383B2

(12) United States Patent
Hall et al.

(10) Patent No.: US 9,958,383 B2
(45) Date of Patent: May 1, 2018

(54) RANGE CAMERA

(71) Applicant: Microsoft Technology Licensing, LLC., Redmond, WA (US)

(72) Inventors: Michael Anthony Hall, Bellevue, WA (US); Kameron Rausch, Sammamish, WA (US); Abdelrehim Ahmed, Santa Clara, CA (US); Beibei Cheng, Redmond, WA (US); Ben Walker, Seattle, WA (US); Jonathan Hoof, Kenmore, WA (US); Daniel Kennett, Bellevue, WA (US)

(73) Assignee: Microsoft Technology Licensing, LLC., Redmond, WA (US)

( * ) Notice: Subject to any disclaimer, the term of this patent is extended or adjusted under 35 U.S.C. 154(b) by 440 days.

(21) Appl. No.: 14/574,451

(22) Filed: Dec. 18, 2014

(65) Prior Publication Data

US 2016/0178512 A1 Jun. 23, 2016

(51) Int. Cl.
| | |
|---|---|
| *G01S 7/497* | (2006.01) |
| *G01S 17/89* | (2006.01) |
| *G01N 21/47* | (2006.01) |
| *G01S 17/46* | (2006.01) |
| *A61B 5/00* | (2006.01) |
| *G01S 17/00* | (2006.01) |

(52) U.S. Cl.
CPC ........... *G01N 21/4738* (2013.01); *A61B 5/44* (2013.01); *G01N 21/4785* (2013.01); *G01S 7/497* (2013.01); *G01S 17/46* (2013.01); *G01S 17/89* (2013.01); *A61B 5/0077* (2013.01); *A61B 5/441* (2013.01); *G06T 2207/10028* (2013.01)

(58) Field of Classification Search
CPC ........... G01N 21/4738; G01N 21/4785; G01N 2223/506; G06T 2207/10028; G06T 7/003; G06T 7/0057; G06T 7/70; G06T 7/73; G06T 7/74; G06T 7/75; G06T 7/77; G01S 17/46; G01S 17/89; G01S 7/497; G01B 11/022; G01C 11/00
USPC ......................................................... 348/135
See application file for complete search history.

(56) References Cited

U.S. PATENT DOCUMENTS

| | | | | |
|---|---|---|---|---|
| 5,838,428 | A * | 11/1998 | Pipitone | ................. G01S 17/89 356/3.09 |
| 6,639,594 | B2 * | 10/2003 | Zhang | ................... G06T 15/506 345/426 |

(Continued)

FOREIGN PATENT DOCUMENTS

GB        2458927 A        10/2009

OTHER PUBLICATIONS

"Second Written Opinion Issued in PCT Application No. PCT/US2015/063568", dated Aug. 5, 2016, 4 Pages.

(Continued)

*Primary Examiner* — Christopher S Kelley
*Assistant Examiner* — Kathleen Walsh
(74) *Attorney, Agent, or Firm* — A.C. Entis-IP Ltd.

(57) ABSTRACT

An active illumination range camera that acquires a range and a picture image of a scene and provides a reflectance for a feature in the scene responsive to a distance for the feature provided by the range image, a registered irradiance for the feature provided by the picture image and registered irradiance for a region of a calibration surface corresponding to the feature provided by an image of the calibration surface acquired by the range camera.

23 Claims, 4 Drawing Sheets

(56) References Cited

U.S. PATENT DOCUMENTS

| | | | | |
|---|---|---|---|---|
| 6,876,392 B1* | 4/2005 | Uomori | G01S 7/481 | |
| | | | 348/347 | |
| 8,049,163 B1 | 11/2011 | Granneman et al. | | |
| 8,130,292 B2* | 3/2012 | Lee | H04N 5/2354 | |
| | | | 348/251 | |
| 8,194,149 B2 | 6/2012 | Thomas et al. | | |
| 9,007,457 B2* | 4/2015 | Levesque | G06T 7/0073 | |
| | | | 348/128 | |
| 2003/0137646 A1* | 7/2003 | Hoffman | G01C 3/08 | |
| | | | 356/4.01 | |
| 2004/0070565 A1* | 4/2004 | Nayar | G06K 9/4661 | |
| | | | 345/156 | |
| 2004/0201586 A1* | 10/2004 | Marschner | G06K 9/4661 | |
| | | | 345/426 | |
| 2004/0263510 A1* | 12/2004 | Marschner | G06T 13/40 | |
| | | | 345/419 | |
| 2010/0026850 A1* | 2/2010 | Katz | G01S 17/89 | |
| | | | 348/234 | |
| 2010/0053592 A1* | 3/2010 | Yahav | G01S 7/486 | |
| | | | 356/4.01 | |
| 2011/0149041 A1 | 6/2011 | Eccles et al. | | |
| 2011/0176709 A1* | 7/2011 | Park | G06T 7/521 | |
| | | | 382/106 | |
| 2011/0211066 A1* | 9/2011 | Fujiki | H04N 7/181 | |
| | | | 348/135 | |
| 2012/0098976 A1* | 4/2012 | Matsushita | H04N 17/002 | |
| | | | 348/187 | |
| 2013/0100250 A1* | 4/2013 | Raskar | H04N 13/02 | |
| | | | 348/46 | |
| 2014/0002610 A1* | 1/2014 | Xi | G01B 11/2513 | |
| | | | 348/46 | |
| 2014/0085625 A1 | 3/2014 | Ahmed et al. | | |
| 2014/0112574 A1 | 4/2014 | Kim et al. | | |
| 2014/0118501 A1 | 5/2014 | Kim et al. | | |

OTHER PUBLICATIONS

Raposo, et al., "Fast and Accurate Calibration of a Kinect Sensor", In Proceedings of International Conference on 3D Vision, Jun. 29, 2013, 8 pages.

Park, et al., "Real Time Rectification Using Differentially Encoded Lookup Table", In Proceedings of the 5th International Conference on Ubiquitous Information Management and Communication, Feb. 21, 2011, 4 pages.

Herrera C, et al., "Joint Depth and Color Camera Calibration with Distortion Correction", In IEEE Transactions on Pattern Analysis and Machine Intelligence, vol. 34, Issue 10, May 29, 2012, 8 pages.

"Computer Vision Group", Published on: Jun. 18, 2012, Available at: https://vision.in.tum.de/data/datasets/rgbd-dataset/file_formats.

"Depth Biomechanics", Published on: Jan. 27, 2014, Available at: http://www.depthbiomechanics.co.uk/?p=2659.

Ellmauthaler, et al., "A Novel Iterative Calibration Approach for Thermal Infrared Cameras", In 20th IEEE International Conference on Image Processing, Sep. 15, 2013, pp. 2182-2186.

"openni_launch/ Tutorials/ Extrinsic Calibration", Retrieved on: Oct. 6, 2014, Available at: http://wiki.ros.org/openni_launch/Tutorials/ExtrinsicCalibration.

Dunne, et al., "Efficient Generic Calibration Method for General Cameras with Single Centre of Projection", In IEEE 11th International Conference on Computer Vision, Oct. 14, 2007, 8 pages.

Abdo, et al., "3D Camera Calibration", Retrieved on: Oct. 6, 2014, Available at: http://ais.informatik.uni-freiburg.de/teaching/ws09/robotics2/projects/mr2-p4-paper.pdf.

Fuchs, et al., "Extrinsic and Depth Calibration of ToF-Cameras", In IEEE Conference on Computer Vision and Pattern Recognition, Jun. 23, 2008, 6 pages.

McIlroy, et al., "Kinectrack: Agile 6-DoF Tracking Using a Projected Dot Pattern", In IEEE International Symposium on Mixed and Augmented Reality, Nov. 5, 2012, 7 pages.

Staranowicz, et al., "Easy-to-Use and Accurate Calibration of RGB-D Cameras from Spheres", In Proceedings of Image and Video Technology—6th Pacific-Rim Symposium, Oct. 28, 2013, 14 pages.

U.S. Appl. No. 14/055,897, filed Oct. 17, 2013.

International Search Report and Written Opinion issued in PCT Application No. PCT/US2015/063568, dated Mar. 3, 2016, 11 Pages.

"International Preliminary Report on Patentability Issued in PCT Application No. PCT/US2015/063568", dated Mar. 30, 2017, 5 Pages.

* cited by examiner

RANGE CAMERA

BACKGROUND

A range camera acquires distances to features in a scene that the range camera images and provides the distances in a range image. Typically, the range camera is an active lighting range camera and comprises a light source that the camera controls to transmit light to illuminate the scene. The range camera images light that the features reflect from the transmitted light back to the camera on pixels of a photosensor that the camera comprises to provide data which may be processed to determine the distances and generate the range image. In a time of flight range camera the camera provides the range image by determining how long it takes the transmitted light that is reflected and imaged on the pixels to make a round trip from the camera to the features and back to the camera. The camera uses the round trip times and the speed of light to determine the distances. In a stereo range camera, the camera provides the range image by determining binocular disparity for features in the scene responsive to the transmitted light that is reflected and imaged on the pixels. The camera triangulates the features responsive to their disparity to determine the distances. Usually, the transmitted light is infrared light (IR). In addition to a range image of a scene, a range camera may also provide a contrast image, a "picture image", of the scene responsive to intensity of the transmitted light that is reflected by the features of the scene and reaches the camera. The picture image provides recognizable images of features in the scene and is advantageous for identifying the features for which the range image provides distances. The picture image and range image of a scene may be acquired by imaging the scene on a same photosensor or on different photosensors registered to each other.

SUMMARY

An aspect of an embodiment of the disclosure relates to providing a range camera that provides a reflectance image of a scene for which the range camera acquires a range image and a picture image. The reflectance image provides a reflectance for features in the scene imaged on pixels of the range camera photosensor for which the range camera provides distances.

To provide the reflectance for the features in the scene, the camera is calibrated in accordance with the disclosure by imaging under known calibration imaging conditions a "calibration surface" having known reflectance on a photosensor of the range camera to acquire a "calibration image". The calibration image comprises measures of amounts of light that pixels in the photosensor register responsive to irradiation by light from regions of the calibration surface imaged on the pixels under the calibration conditions. An amount of light that a pixel registers from a region of the calibration surface may be referred to as registered calibration irradiance (RCI). A reflectance of a given feature of the scene imaged on a pixel of the range camera photosensor in the picture image is determined responsive to an amount of light, hereinafter also referred to as registered scene irradiance (RSI), registered by the pixel for the given feature in the picture image, distance of the feature from the camera determined from a range image of the scene, and the RCI of a corresponding pixel in the calibration image. The corresponding pixel is a pixel that images a region of the calibration surface corresponding to the given feature. The corresponding region of the calibration surface is a region that the range camera illuminates to acquire the calibration image along a same direction that the range camera illuminates the given feature of the scene to acquire the picture image of the scene. The RCI for a corresponding pixel on which the corresponding calibration region is imaged in the calibration image is used to normalize the RSI to provide a reflectance for the region of the scene and a reflectance image of the scene.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

In the following detailed description a method of operating a range camera to acquire a calibration image of an optionally planar calibration surface in accordance with an embodiment of the disclosure is discussed with reference to FIG. 1. A method of using the calibration image to determine reflectance of a region of a scene imaged by the range camera in accordance with an embodiment of the disclosure is described with reference to FIG. 2A. In FIG. 2A the region of the scene for which reflectance is determined is, by way of example, parallel to the calibration surface shown in FIG. 1. How the method may be modified to determine reflectance for a region of the scene tilted with respect to the calibration surface, in accordance with an embodiment of the disclosure, is discussed with reference to FIG. 2B. FIG. 3 schematically shows a human computer interface comprising a range camera that operates to determine a user's facial reflectance in accordance with an embodiment of the disclosure. In the discussion, characters in bold script represent a vector. The characters in normal script represent the absolute value of the vector. A character in bold script accented by a cap represents a unit vector.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

It is noted that methods of providing a range camera with a calibration image and using the calibration image to determine reflectivity of features of a scene imaged by the camera in accordance with an embodiment of the disclosure are substantially independent of camera design and how the range camera determines distance to the features. Different range cameras calibrated and operated in accordance with an embodiment of the disclosure may therefore be expected to provide same reflectance images for a same scene substantially independent of how the range cameras operate to acquire range and picture images of the scene. The reflectance images may also be expected to be substantially independent of imaging conditions, such as, for a same spectrum, intensity of illumination of the scene and distances of the cameras from the scene.

As a result, image processing algorithms that process images of scenes acquired by a range camera calibrated in accordance with an embodiment of the disclosure to provide functionalities that may be responsive to reflectance of features in the scenes may be generic to range camera types. That is, the image processing algorithms may process a reflectance image of a scene to provide functionalities substantially in a same way and provide substantially a same result independent of type and design of a range camera that provides the image and/or imaging conditions under which the range camera acquired the image. Among functionalities responsive to reflectance of features that the image processing algorithms may advantageously provide include by way of example, person identification, gesture recognition, determination of emotional or physiological state from changes in skin tone, and avatar generation.

Figure 1:
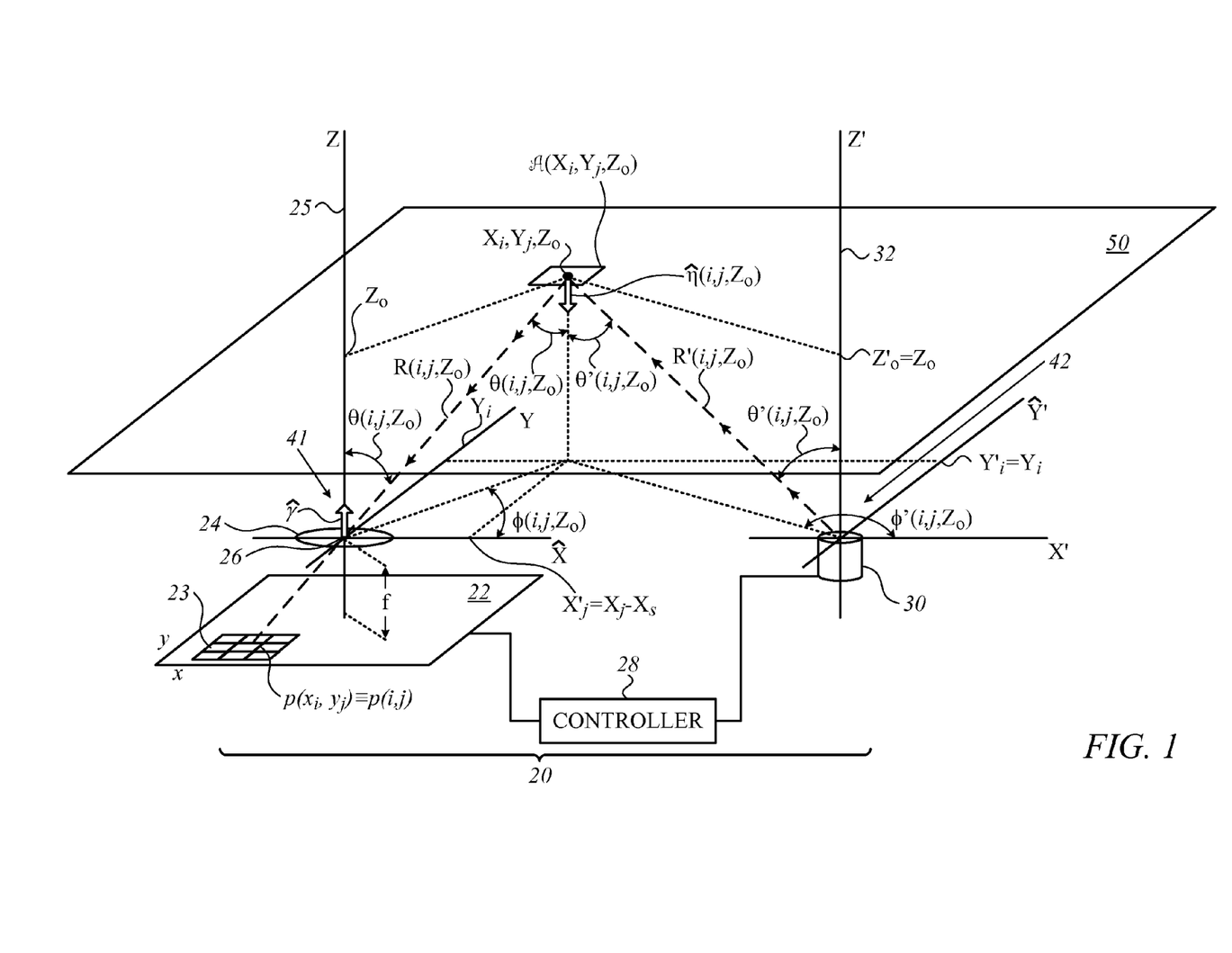
FIG. 1 schematically shows calibrating a range camera in accordance with an embodiment of the disclosure.
Figure 2A:
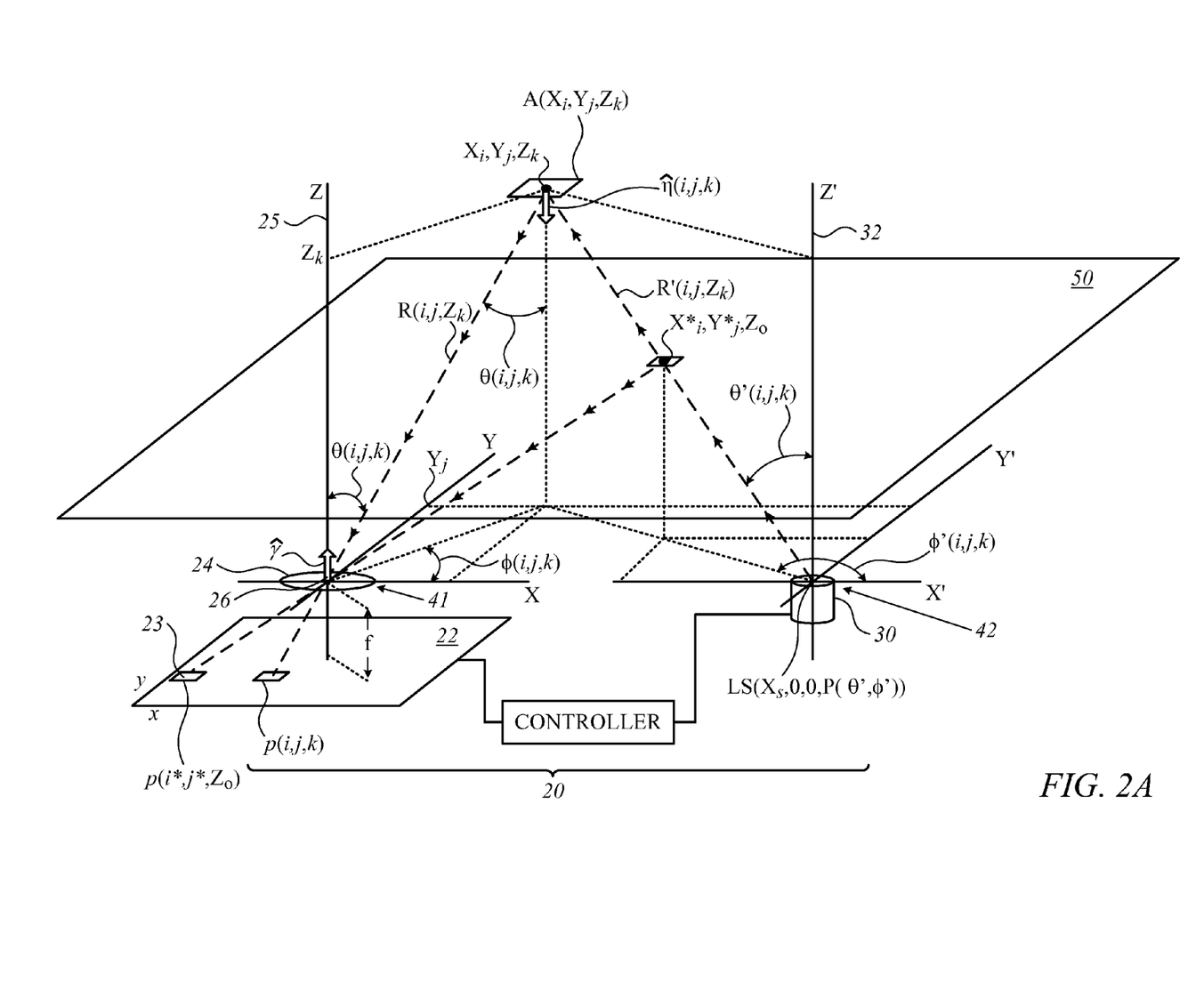
FIG. 2A schematically shows the range camera shown in FIG. 1 determining reflectance for a region of a scene perpendicular to an optic axis of the range camera, in accordance with an embodiment of the disclosure.

FIG. 1 schematically shows a range camera 20 imaging a calibration surface 50 under calibration imaging conditions to acquire a calibration image for use in determining reflectance of features in a scene that the camera images, in accordance with an embodiment of the disclosure. Range camera 20 is shown very simplified and may operate in accordance with any of various methods for determining distances to features in a scene that the range camera images and providing a range image of the scene responsive to the determined distances. Range camera 20 optionally determines distances to the features by time of flight and/or triangulation.

Optionally, range camera 20 comprises a light source 30 controllable to transmit, optionally infrared (IR) light to illuminate features in a scene the camera images, a photosensor 22 having pixels 23, and an optical system, which is represented by, and referred to as, a lens 24. Lens 24 collects light reflected by the features from light transmitted by light source 30 and images the reflected light onto pixels 23 of photosensor 22. The lens has an optical axis 25, optical center 26 and a diameter "D" that optionally defines an optical aperture, $\alpha=\pi D^2/4$, of the lens and the optical system the lens represents. A unit vector $\hat{\gamma}$ lies along, and represents a direction of optical axis 25. Photosensor 22 is substantially perpendicular to optical axis 25 and located at a focal distance, "f", from optical center 26. A pixel 23 comprised in photosensor 22 is located in the photosensor by pixel coordinates measured long x and y axes shown along edges of the photosensor. A pixel coordinate origin from which pixel coordinates may be measured is located at an intersection of optical axis 25 and photosensor 22. A pixel located at pixel coordinates $x_i$ and $y_j$ may be represented by $p(x_i, y_j)$ or $p(i,j)$.

A controller 28 controls operation of range camera 20. The controller may by way of example, control intensity and modulation of light that light source 30 transmits to illuminate features in an imaged scene and shuttering of the camera to provide desired exposure periods for imaging transmitted light that is reflected by the features back to the range camera on pixels 23. Controller 28 may process light reflected by the features and registered by pixels 23 during the exposure periods to determine distances to the features and therefrom a range image of the scene and/or a picture image of the scene.

A pixel in a range camera, such as a pixel 23 in photosensor 22, registers incident light that irradiates the pixel by accumulating positive or negative electric charge, also referred to as "photocharge", provided by electron-hole pairs generated by photons in the incident light. Circuitry in the range camera may convert photocharge accumulated by the pixels into voltages that are used as measures of the amounts of photocharge they respectively accumulate and thereby of irradiance of the pixels. An amount of light that a pixel registers, also referred to as registered irradiance, may refer to an amount of optical energy that irradiates the pixel, an amount of photocharge accumulated by a pixel responsive to irradiance, or to any representation of the accumulated photocharge such as a voltage, current, or digital data generated responsive to the accumulated photocharge.

Spatial locations of features in a field of view (FOV) of range camera 20 relative to the range camera are defined by spatial coordinates measured along X, Y, and Z axes of an optionally Cartesian coordinate system 41. The Z axis is optionally coincident with optical axis 25 of range camera 20. Light source 30 is located along the X axis at a distance $X_S$ from optical center 26 and has an illumination axis 32, which is optionally parallel to optical axis 25 and intersects the X axis at a distance $X_S$. Spatial locations of features in the FOV of range camera 20 relative to light source 30 may be defined by spatial coordinates measured along "primed" axes X', Y', and Z' of a primed coordinate system 42. Optionally, the Z' axis is coincident with illumination axis 32, and the X' and Y' axes are respectively parallel to the X and Y axes. Origins of coordinate systems 41 and 42 may be considered to be, and may be referred to as, the locations of lens 24 and light source 30.

Calibration surface 50 is optionally planar, and has a known reflectance "$\rho_o$", which, optionally, is the same for substantially all regions of the calibration surface. The calibration conditions under which range camera 20 images calibration surface 50 optionally comprise a known distance and orientation of calibration surface 50 relative to the range camera optical axis 25, known range camera settings, such as aperture and exposure period, and a known optical output power with which light source 30 illuminates the calibration surface. By way of example, in FIG. 1 calibration surface 50 is perpendicular to optical axis 25, and is located at a distance $Z_o$ from optical center 26 along the Z axis.

Let a region of calibration surface 50 imaged on a given pixel p(i,j,) shown in FIG. 1 be represented by $\mathcal{A}(X_i, Y_j, Z_o)$, where $X_i$ and $Y_j$ are X and Y coordinates of region $\mathcal{A}(X_i, Y_j, Z_o)$ in coordinate system 41. Coordinates $X_i$ and $Y_j$ correspond to coordinates $x_i$, $y_j$ of pixel p(i,j) in photosensor 22 and lie along a line that extends from substantially a central point in region $\mathcal{A}(X_i,Y_j,Z_o)$, passes through optic center 26 and ends substantially at a central point in pixel p(i,j). Coordinate $x_i=-(f/Z_o)X_i$ and coordinate $y_j=-(f/Z_o)Y_j$. Pixel p(i,j) on which $\mathcal{A}(X_i,y_j,Z_o)$ is imaged may be represented by p(i,j,$Z_o$) to associate the pixel with $\mathcal{A}(X_i,Y_j,Z_o)$, and to indicate that the feature, region $\mathcal{A}(X_i,Y_j,Z_o)$, imaged on the pixel is located at Z coordinate $Z_o$.

$\mathcal{A}(X_i,Y_j,Z_o)$ is located at a distance defined by a distance vector, "R(i,j,$Z_o$)" that extends from optical center 26 to coordinates $X_i,Y_j,Z_o$ at a zenith angle $\theta(i,j,Z_o)$ relative to the Z axis of coordinate system 41 and at an azimuth angle $\varphi(i,j,Z_o)$ relative to the X axis of the coordinate system. The absolute value of $|R(i,j,Z_o)| \equiv R(i,j,Z_o)=[X_i^2+Y_j^2+Z_o^2]^{1/2}$. In primed coordinate system 42, region $\mathcal{A}(X_i,Y_j,Z_o)$ has coordinates $X'_i=(X_i-X_S)$, $Y'_j=Y_j$, and $Z'=Z_o$, and is located at distance defined by a distance vector R'(i,j,$Z_o$) directed from light source 30 at a zenith angle $\theta'(i,j,Z_o)$ relative to the Z' axis and at an azimuth angle $\varphi'(i,j,Z_o)$ relative to the X' axis. $|R'(i,j,Z_o)| \equiv R'(i,j,Z_o)=[X'^2_i+Y'^2_j+Z'^2_o]^{1/2}=[X_i-X_S)^2+Y_j^2+Z_o^2]^{1/2}$. Arrows along distance vectors R(i,j,$Z_o$) and R'(i,j,$Z_o$) indicate direction of propagation of light from light source 30 to region $\mathcal{A}(X_i,Y_j,Z_o)$ and therefrom to pixel p(i,j) of photosensor 22. A unit normal to $\mathcal{A}(X_i,Y_j,Z_o)$ is represented by $\hat{\eta}(i,j,Z_o)$. If "$A_p$" represents the area of a pixel p(i,j), and $\mathcal{A}(i,j,Z_o)$ the area of region $\mathcal{A}(X_i,Y_j,Z_o)$, then, $$\mathcal{A}(i,j,Z_o)=A_p(Z_o/f)^2. \quad (1)$$

If, under calibration conditions, optical power per unit solid angle of light that light source 30 transmits in a direction defined by a given zenith angle $\theta'$ and azimuth angle $\varphi'$ is represented by a vector $P_o(\theta',\varphi')$, then optical power per unit solid angle that light source 30 transmits in the direction of $\mathcal{A}(X_i,Y_j,Z_o)$ is $P_o(\theta'(i,j,Z_o),\varphi'(i,j,Z_o))$, which, for convenience, may also be written $P_o(\theta',\varphi',(i,j,Z_o))$. A total amount of optical power, hereinafter also referred to as "total irradiance" (TIR), incident on $\mathcal{A}(X_i,Y_j,Z_o)$ from light source 30 under calibration conditions is therefore equal to the area $\mathcal{A}(i,j,Z_o)$ times the scalar product of $\hat{\eta}(i,j,Z_o)$ and $P_o(\theta',\varphi',(i,j,Z_o))$ divided by the square of the distance from light source 30 to $\mathcal{A}(X_i,Y_j,Z_o)$. In symbols, letting TIR($\mathcal{A}(X_i,Y_j,Z_o)$) represent a total irradiance of region $\mathcal{A}(X_i,Y_j,Z_o)$ by light source 30 under calibration conditions, TIR($\mathcal{A}(X_i,Y_j,Z_o)$) may therefore be written:

$$\text{TIR}(\mathcal{A}(X_i,Y_j,Z_o))=\mathcal{A}(i,j,Z_o)\hat{\eta}(i,j,Z_o)\cdot P_o(\theta',\varphi',(i,j,Z_o))/R'(i,j,Z_o)^2, \quad (2)$$

where "·" indicates a scalar product.

Since calibration plane 50 is assumed parallel to photosensor 22, $\hat{\eta}(i,j,Z_o)$ is parallel to axis Z and axis Z' and, $$\hat{\eta}(i,j,Z_o) \cdot P_o(\theta',\varphi',(i,j,Z_o))=P_o(\theta',\varphi',(i,j,Z_o))\cos\theta'(i,j,Z_o)$$
$$=P_o(\theta',\varphi',(i,j,Z_o))[Z_o/R'(i,j,Z_o)]. \quad (3)$$

The expression for TIR($\mathcal{A}(X_i,Y_j,Z_o)$) in equation (2) may therefore be written, $$\text{TIR}(\mathcal{A}(X_i,Y_j,Z_o))=\mathcal{A}(i,j,Z_o)P_o(\theta',\varphi',(i,j,Z_o))[Z_o/R'(i,j,Z_o)^3]. \quad (4)$$

Substituting the expression for $\mathcal{A}(i,j,Z_o)$ from equation (1) provides $$\text{TIR}(\mathcal{A}(X_i,Y_j,Z_o)) = A_p(Z_o/f)^2 P_o(\theta',\varphi',(i,j,Z_o))[Z_o/R'(i,j,Z_o)^3] \quad (5)$$
$$= (A_p/f^2)P_o(\theta',\varphi'(i,j,Z_o))[Z_o/R'(i,j,Z_o)]^3.$$

Assuming that $\mathcal{A}(i,j,Z_o)$ is a diffuse reflector that reflects light with equal optical power per unit solid angle in all directions in a hemisphere centered on $\mathcal{A}(i,j,Z_o)$ and facing range camera 20, $\mathcal{A}(i,j,Z_o)$ reflects light towards lens 24 along a direction of R(i,j,$Z_o$) defined by zenith and azimuth angles $\theta(i,j,Z_o)$ and $\varphi(i,j,Z_o)$, with "reflected" optical power per solid angle, $$RP_o(\theta,\varphi,(i,j,Z_o))=\hat{R}(i,j,Z_o)\rho_o\text{TIR}(\mathcal{A}(X_i,Y_j,Z_o))/2\pi, \quad (6)$$

where $\hat{R}(i,j,Z_o)$ is a unit vector along R(i,j,$Z_o$) in a direction from $\mathcal{A}(i,j,Z_o)$ to lens 24.

Reflected optical power incident on aperture $\alpha$ of lens 24 from region $\mathcal{A}(X_i,Y_j,Z_o)$, that is total irradiance, TIR($\alpha, \mathcal{A}(X_i,Y_j,Z_o)$), of lens 24 by reflected light from $\mathcal{A}(X_i,Y_j,Z_o)$ may therefore be given by an expression:

$$\text{TIR}(\alpha, \mathcal{A}(X_i, Y_j, Z_o)) = (\alpha/R(i,j,Z_o)^2)\hat{\gamma}\cdot RP_o(\theta,\varphi,(i,j,Z_o)) \quad (7)$$
$$= (\alpha/R(i,j,Z_o)^2)\hat{\gamma}\cdot$$
$$\hat{R}(i,j,Z_o)\rho_o\text{TIR}(\mathcal{A}(X_i,Y_j,Z_o))/2\pi,$$

where $(\alpha/R(i,j,Z_o)^2)\hat{\gamma}\cdot\hat{R}(i,j,Z_o)$ is a solid angle subtended by aperture $\alpha$ at $\mathcal{A}(X_i,Y_j,Z_o)$. Noting that $\hat{\gamma}\cdot\hat{R}(i,j,Z_o)=\cos\theta(i,j,Z_o)=Z_o/R(i,j,Z_o)$, expression (7) may be rewritten:

$$\text{TIR}(\alpha,\mathcal{A}(X_i,Y_j,Z_o))=(\alpha Z_o/R(i,j,Z_o)^3)\rho_o\text{TIR}(\mathcal{A}(X_i,Y_j,Z_o))/2\pi. \quad (8)$$

Using the expression for TIR($\mathcal{A}(X_i,Y_j,Z_o)$) given by equation (5), and rearranging terms, equation (8) becomes, $$\text{TIR}(\alpha,\mathcal{A}(X_i,Y_j,Z_o))=\rho_o(A_p\alpha/2\pi f^2)Z_o^4 P_o(\theta',\varphi',(i,j,Z_o))[R(i,j,Z_o)R'(i,j,Z_o)]^{-3}. \quad (9)$$

Let $\tau$, represent a coefficient that relates optical power, TIR($\alpha, \mathcal{A}(X_i,Y_j,Z_o)$), incident on pixel p(i,j) to the registered calibration irradiance RCI(i,j,$Z_o$), that the pixel provides as a measure of total irradiance TIR($\alpha, \mathcal{A}(X_i,Y_j,Z_o)$). RCI(i,j,$Z_o$), may be given by the equation:

$$RCI(i,j,Z_o) = \tau\text{TIR}(\alpha,\mathcal{A}(X_i,Y_j,Z_o)) \quad (10)$$
$$= \tau\rho_o(A_p\alpha/2\pi f^2)Z_o^4 P_o(\theta',\varphi'(i,j,Z_o))$$
$$[R(i,j,Z_o)R'(i,j,Z_o)]^{-3}.$$

Measurements RCI(i,j,$Z_o$) acquired for a plurality of pixels p(i,j,$Z_o$) that image different regions $\mathcal{A}(X_i,Y_j,Z_o)$ of calibration surface 50 provide a calibration image for range camera 20. The calibration image may be used to determine reflectances of features in a scene imaged in a picture image of the scene acquired by range camera 20, in accordance with an embodiment of the disclosure as described below.

FIG. 2A schematically shows range camera 20 imaging a feature, a region A($X_i,Y_j,Z_k$) of a scene (not shown), to acquire a picture image of the scene and determine reflectance of the region. A($X_i,Y_j,Z_k$) is located at coordinates $X_i,Y_j,Z_k$ of coordinate system 41, has an unknown reflectance $\rho(i,j,k)$ and has a unit normal $\hat{\eta}(i,j,Z_k)$, which may be written $\hat{\eta}(i,j,k)$, parallel to optic axis 25. Region A($X_i,Y_j,Z_k$) has an area A(i,j,$Z_k$)=$A_p(Z_k/f)^2$, is located at a distance defined by a distance vector R(i,j,$Z_k$) that extends from light source 30 at a zenith angle $\theta(i,j,k)$ relative to the Z axis and at an azimuth angle $\varphi(i,j,k)$ relative to the X axis. $|R(i,j,Z_k)|\equiv R(i,j,Z_k)=[X_i^2+Y_j^2+Z_k^2]^{1/2}$. Region A($X_i,Y_j,Z_k$), is imaged on a pixel p(i,j,k) of photosensor 22. With respect to coordinate system 42, region A($X_i,Y_j,Z_k$) is located at coordinates $X'_i=(X_i-X_S)$, $Y'_j=Y_j$, and $Z'=Z_k$ determined by a distance vector R'(i,j,$Z_k$) extending from light source 30 at zenith and azimuth angles $\theta'(i,j,k)$ and $\varphi'(i,j,k)$ respectively. $|R'(i,j,Z_k)| \equiv R'(i,j,Z_k) = [X'^2_i + Y'^2_j + Z'^2_k]^{1/2} = [(X_i - X_S)^2 + Y^2_j + Z^2_k]^{1/2}$. Arrows along distance vectors $R(i,j,Z_k)$ and $R'(i,j,Z_k)$ schematically indicate propagation of light from light source 30 to pixel p(i,j,k). It is noted that when range camera 20 images the scene comprising region $A(X_i,Y_j,Z_k)$, calibration surface 50 is not present and is shown in FIG. 2A to show geometrical relationships between region $A(X_i,Y_j,Z_k)$ and regions of the calibration surface.

Let an amount of light, that is, registered scene irradiance RSI, that pixel p(i,j,k) registers for light from region $A(X_i,Y_j,Z_k)$ when acquiring the picture image of the scene comprising $A(X_i,Y_j,Z_k)$ be represented by "RSI(i,j,$Z_k$)". Assume that controller 28 operates light source 30 to illuminate the scene with optical power $P_o(\theta',\varphi',(i,j,Z_o))$. Then, similar to determining RCI(i,j,$Z_o$) in accordance with equation (10) for pixel p(i,j,$Z_o$) that images region $\mathcal{A}(X_i,Y_j,Z_o)$ of calibration surface 50 under calibration conditions, RSI(i,j,$Z_k$), may be determined by an equation:

$$RSI(i,j,Z_k) = \tau\rho(i,j,k)(A_p\alpha/2\pi f^2)Z_k^4 P_o(\theta',\varphi',(i,j,Z_k))[R(i,j,Z_k)R'(i,j,Z_k)]^{-3}. \quad (11)$$

To determine $\rho(i,j,k)$ for $A(X_i,Y_j,Z_k)$ according to an embodiment of the disclosure, controller 28 controls range camera 20 to acquire a range image for the scene comprising region $A(X_i,Y_j,Z_k)$ to determine a distance, $R(i,j,Z_k)$, from the range camera to region $A(X_i,Y_j,Z_k)$. The controller uses distance $R(i,j,Z_k)$, $RSI(i,j,Z_k)$ provided by pixel p(i,j,k) for $A(X_i,Y_j,Z_k)$, and a $RCI(i,j,Z_o)$ acquired for a pixel that images a region of calibration surface 50 in the calibration image acquired for range camera 20 that corresponds to region $A(X_i,Y_j,Z_k)$ to determine reflectance $\rho(i,j,k)$.

In an embodiment of the disclosure, a region of calibration surface 50 that corresponds to region $A(X_i,Y_j,Z_k)$ comprises a region of the calibration surface that is illuminated by light from light source 30 when imaged by range camera 20 to acquire the calibration image along substantially a same direction along which light from light source 30 illuminates region $A(X_i,Y_j,Z_k)$ to acquire the picture image of the scene comprising an image of $A(X_i,Y_j,Z_k)$. In an embodiment of the disclosure, the corresponding region is a region $\mathcal{A}(X^*_i,Y^*_j,Z_o)$ shown in FIG. 2A having coordinates $X^*_i,Y^*_j,Z_o$ in coordinate system 41 that is imaged on a pixel p(i*,j*,$Z_o$) of photosensor 22, and through which distance vector $R'(i,j,Z_k)$ passes. Coordinates $X_i,Y_j$, and $Z_k$ for $A(X_i,Y_j,Z_k)$ provided by range camera 20 from coordinates of pixel p(i,j,k) on which the range camera images $A(X_i,Y_j,Z_k)$, may be used to determine coordinates $X^*_i,Y^*_j$ in accordance with the following equations:

$$X^*_i = X_i + (1-(Z_o/Z_k))X_S \text{ and } Y^*_j = (Z_o/Z_k)Y_j, \quad (12)$$

Using equations (12), the coordinates $x_i^*$ and $y_j^*$ of pixel p(i*,j*,$Z_o$) may be written $$x_i^* = -(f/Z_o)X^*_i \text{ and } y_j^* = -(f/Z_o)Y^*_j. \quad (13)$$

The determined coordinates $x_i^*$ and $y_j^*$ identify a pixel p(i*,j*, $Z_o$) that provides a registered calibration irradiation, $RCI(i^*,j^*,Z_o)$, for region $\mathcal{A}(X^*_i,Y^*_j,Z_o)$ corresponding to region $A(X_i,Y_j,Z_k)$. In accordance with an embodiment of the disclosure, $RCI(i^*,j^*,Z_o)$ is used to determine $\rho(i,j,k)$ for region $A(X_i,Y_j,Z_k)$ as described below.

From equation (10), $$RCI(i^*,j^*,Z_o) = (\tau\rho_o A_p\alpha/2\pi f^2)Z_o^4 P_o(\theta',\varphi',(i^*,j^*,Z_o))[R(i^*,j^*,Z_o)R'(i^*,j^*,Z_o)]^{-3}. \quad (14)$$

where $R(i^*,j^*,Z_o) = [X^{*2}_{i*} + Y^{*2}_{j*} + Z_o^2]^{1/2}$ and $R'(i^*,j^*,Z_o) = [(X_{i*} - X_S)^2 + Y^{*2}_{j*} + Z^{*2}_{o*}]^{1/2}$. In expression (14) $P_o(\theta',\varphi',(i^*,j^*,Z_o))$ is the magnitude of the optical power per unit solid angle that light source 30 transmits in the direction of region $A(X_i,Y_j,Z_k)$ to illuminate $A(X_i,Y_j,Z_k)$ with light. Rearranging equation (11) provides an equation for reflectance $\rho(i,j,k)$ of $A(X_i,Y_j,Z_k)$:

$$\rho(i,j,k) = (\tau A_p\alpha/2\pi f^2)^{-1} Z_k^{-4} [R(i,j,Z_k)R'(i,j,Z_k)]^3 RSI(i,j,Z_k)/P_o(\theta',\varphi',(i,j,Z_k)). \quad (15)$$

Rearranging equation 10 provides an expression for optical power $P_o(\theta',\varphi',(i,j,Z_k))$:

$$P_o(\theta',\varphi',(i^*,j^*,Z_o)) = (2\pi f^2/\tau\rho_o A_p\alpha)RCI(i^*,j^*,Z_o)Z_o^{-4}[R(i^*,j^*,Z_o)R'(i^*,j^*,Z_o)]^3. \quad (16)$$

Substituting the expression for $P_o(\theta',\varphi',(i^*,j^*,Z_o))$ from equation (16) into equation (15) provides an equation that determines $\rho(i,j,k)$:

$$\rho(i,j,k) = \rho_o(Z_o/Z_k)^4 [RSI(i,j,Z_k)/RCI(i^*,j^*,Z_o)][(R(i,j,Z_k)/R(i^*,j^*,Z_o))(R'(i,j,Z_k)/R'(i^*,j^*,Z_o))]^3 \quad (17)$$

Equation (17) determines reflectance for region $A(X_i,Y_j,Z_k)$ in accordance with an embodiment of the disclosure in terms of calibration reflectance $\rho_o$, registered irradiances RSI(i,j,$Z_k$) and RCI(i*,j*,$Z_o$), and spatial coordinates provided by a range image acquired by range camera 20.

An alternative expression for $\rho(i,j,k)$ may be determined by normalizing coordinates $X_i,Y_j$ and $X'_i,Y'_j$ to $Z_o$ and writing equations (10) in terms of pixel coordinates $x_i$ and $y_j$ of a pixel p(i,j) to provide:

$$RCI(i,j,Z_o) = \{\tau(A_p\alpha/2\pi f^2)[1+(x_i/f)^2+(y_j/f)^2]^{-3/2}\}\rho_o P_o(\theta',\varphi',(i,j,Z_o))Z_o^{-2}[1+((x_i/f)-X_S/Z_o)^2+(y_j/f)^2]^{-3/2}. \quad (18)$$

The quantities in curly brackets are constants and independent of $Z_o$ for a given pixel. Representing the quantities in brackets by a constant K(i,j), the expression (18) may be written.

$$RCI(i,j,Z_o) = K(i,j)\rho_o P_o(\theta',\varphi',(i,j,Z_o))Z_o^{-2}[1+((x_i/f)-X_S/Z_o)^2+(y_j/f)^2]^{-3/2}. \quad (19)$$

Similarly, equation (11) for the pixel may be written, $$RSI(i,j,Z_k) = K(i,j)\rho(i,j,k)P_o(\theta',\varphi',(i,j,Z_k))Z_k^{-2}[1+((x_i/f)-X_S/Z_k)^2+(y_j/f)^2]^{-3/2}. \quad (20)$$

As a result, $\rho(i,j,k)$ may be determined in accordance with an expression, $$\rho(i,j,k) = \rho_o[RSI(i,j,Z_k)/RCI(i,j,Z_o,\rho_o)](Z_k^2/Z_o^2)P_o(\theta',\varphi',(i,j,Z_o))/P_o(\theta',\varphi',(i,j,Z_k)) \times [1+((x_i/f)-X_S/Z_k)^2+(y_j/f)^2]^{3/2}/[1+((x_i/f)-X_S/Z_o)^2+(y_j/f)^2]^{3/2}. \quad (21)$$

In general, the term $X_S/Z_k$ and $X_S/Z_o$ are relatively small compared to the other terms in the expressions $[1+((x_i/f)-X_S/Z_k)^2+(y_j/f)^2]$ and $[1+((x_i/f)-X_S/Z_o)^2+(y_j/f)^2]$, and the ratio is $P_o(\theta',\varphi',(i,j,Z_o))/P_o(\theta',\varphi',(i,j,Z_k))$ is a weak function of $Z_k$. The terms following the term $(Z_k^2/Z_o^2)$ in equation (21) may therefore conveniently be expressed as a power series about the coordinate $Z_o$ optionally of the form $(a_o(i,j,Z_o)+a_1(i,j,Z_o)Z_k^{-1}+a_2(i,j,Z_o)Z_k^{-2}...)$ so that $$\rho(i,j,k) = \rho_o[RSI(i,j,Z_k)/RCI(i,j,Z_o,\rho_o)](Z_k^2/Z_o^2)(a_o(i,j,Z_o)+a_1(i,j,Z_o)Z_k^{-1}+...) \quad (22)$$

In an embodiment of the disclosure range camera 20 is calibrated by imaging calibration surface 50 at each of a plurality of different known calibration distances from the range camera to provide calibration images and registered calibration irradiances RCI(i,j,$Z'_o$) for a plurality of known different distances "$Z'_o$" from the range camera. Coefficients for the power series may be determined from the calibration irradiances for each of the distances $Z'_o$. Values of the calibration irradiances RCI(i,j,$Z'_o$) and associated coefficients ($a_o(i,j,Z_o), a_1(i,j,Z_o), ...$) for each pixel may be stored in a look up table (LUT) in controller 28. The controller uses the LUT values for a given pixel p(i,j) to determine a reflectance ρ(i,j,k), optionally in accordance with expression (22) for a feature that range camera 20 images on the given pixel.

In an embodiment, distances between calibration distances $Z'_o$ are determined so that a number of power series coefficients stored in the LUT for a pixel p(i,j) occupies a desired amount of memory in controller 28, and is sufficient to provide values for ρ(i,j,k) for the pixel having desired accuracy in a desired controller processing time. In an embodiment, a number of power coefficients stored per pixel is less than or equal to about 5. Optionally, the number is less than or equal to 2.

In an embodiment of the disclosure each of a plurality of range cameras of a same given type and/or make is calibrated in a calibration procedure in which the range camera is operated to image calibration surface 50 at each of a plurality of known distances to acquire an empirical LUT specific to the camera. Values for irradiances and power series coefficients in the acquired empirical LUTs are suitably average to generate a generic LUT. The generic LUT may be installed in a range camera of the same given type and/or make for use in determining reflectances without having to operate the range camera to acquire an empirical LUT.

In deriving equation (17)-(22) it is assumed that reflectance of calibration surface 50 is the same for all regions of the calibration surface, the calibration surface is planar, and that range camera 20 illuminates the scene comprising $A(X_i, Y_j, Z_k)$ with a same optical power $P_o(\theta',\varphi',(i^*,j^*,Z_o))$ used to acquire a calibration image for the range camera. Embodiments are not limited to planar calibration surfaces having uniform reflectance $\rho_o$. For example, RCIs useable for determining a reflectance ρ(i,j,k) for features in a scene may be determined for a cylindrical or a spherical calibration surface using a modification of equations (17)-(22) that accounts for the non-planar geometry of the calibration surface. And reflectance of calibration surface 50 may for example, be a known, non-constant function $\rho_o(i,j,k)$ of coordinates $X_i, Y_j, Z_k$ on the calibration surface. Nor is practice of an embodiment of the disclosure limited to illuminating a scene with optical power $P_o(\theta',\varphi',(i^*,j^*,Z_o))$. Light source 30 may be operated to illuminate scenes imaged by range camera 20 at different levels of optical power. Equations (17)-(22) may be modified to account for illuminating a scene at an optical power different from $P_o(\theta',\varphi',(i^*,j^*,Z_o))$ by multiplying the right hand side of equation (17) and (22) by a suitable ratio between the different optical power and $P_o(\theta',\varphi',(i^*,j^*,Z_o))$.

It is noted that in the above description, the normal $\hat{\eta}(i,j,Z_o)$ to calibration surface region $\mathcal{A}(X_i,Y_j,Z_o)$, and the normal $\hat{\eta}(i,j,Z_k)$ to scene region $A(X_i,Y_j,Z_k)$ are assumed parallel to optic axis 25 of range camera 20. However, practice of an embodiment of the disclosure is not limited to determining reflectances for scene regions having normals parallel to optic axis 25 and for tilted scene regions a modification of expression (17) may be used to provide reflectances ρ(i,j,k) for the regions.

Figure 2B:
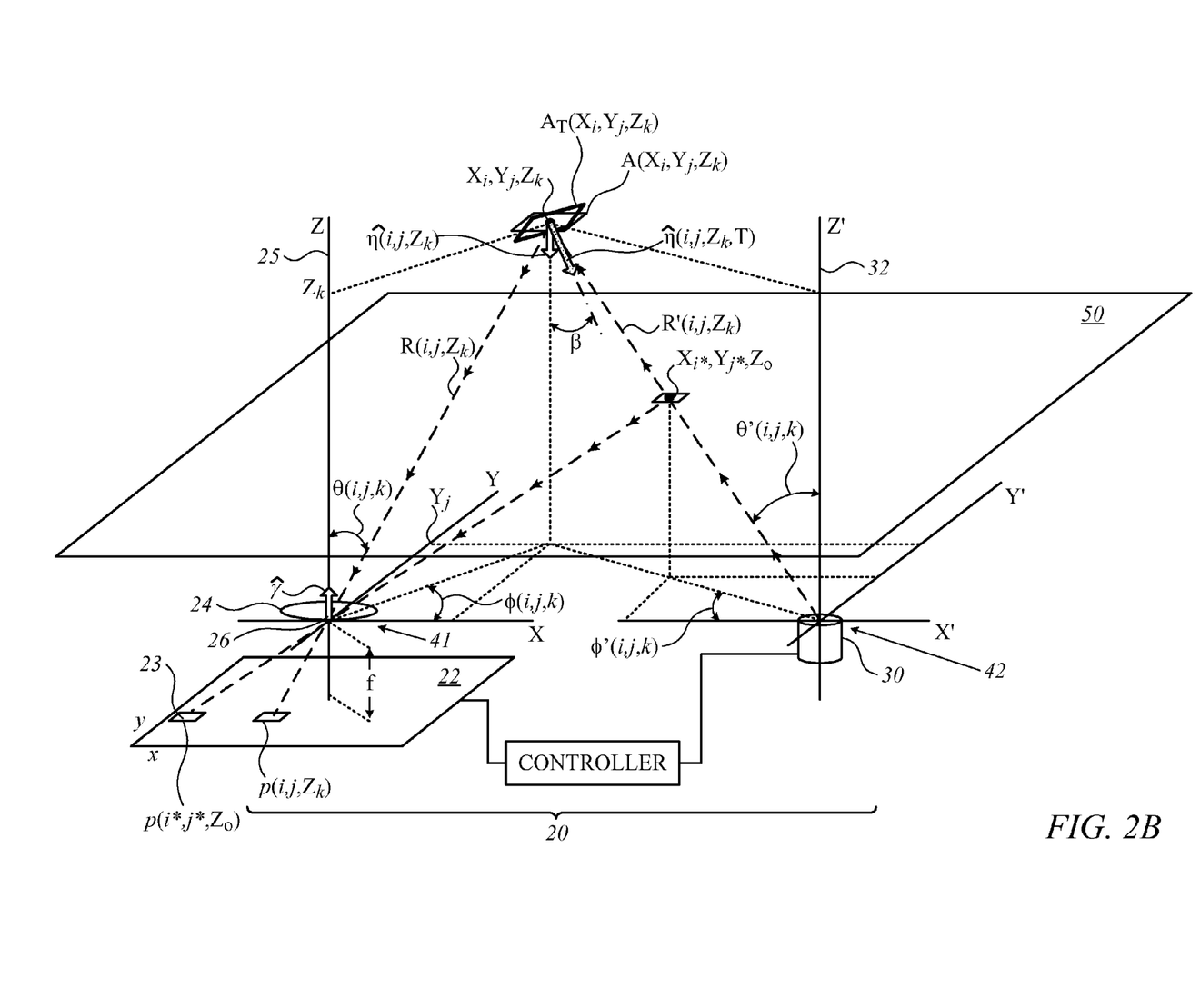
FIG. 2B schematically shows the range camera shown in FIG. 1 determining reflectance for a region of a scene that is not perpendicular to the optical axis in accordance with an embodiment of the disclosure.
Figure 3:
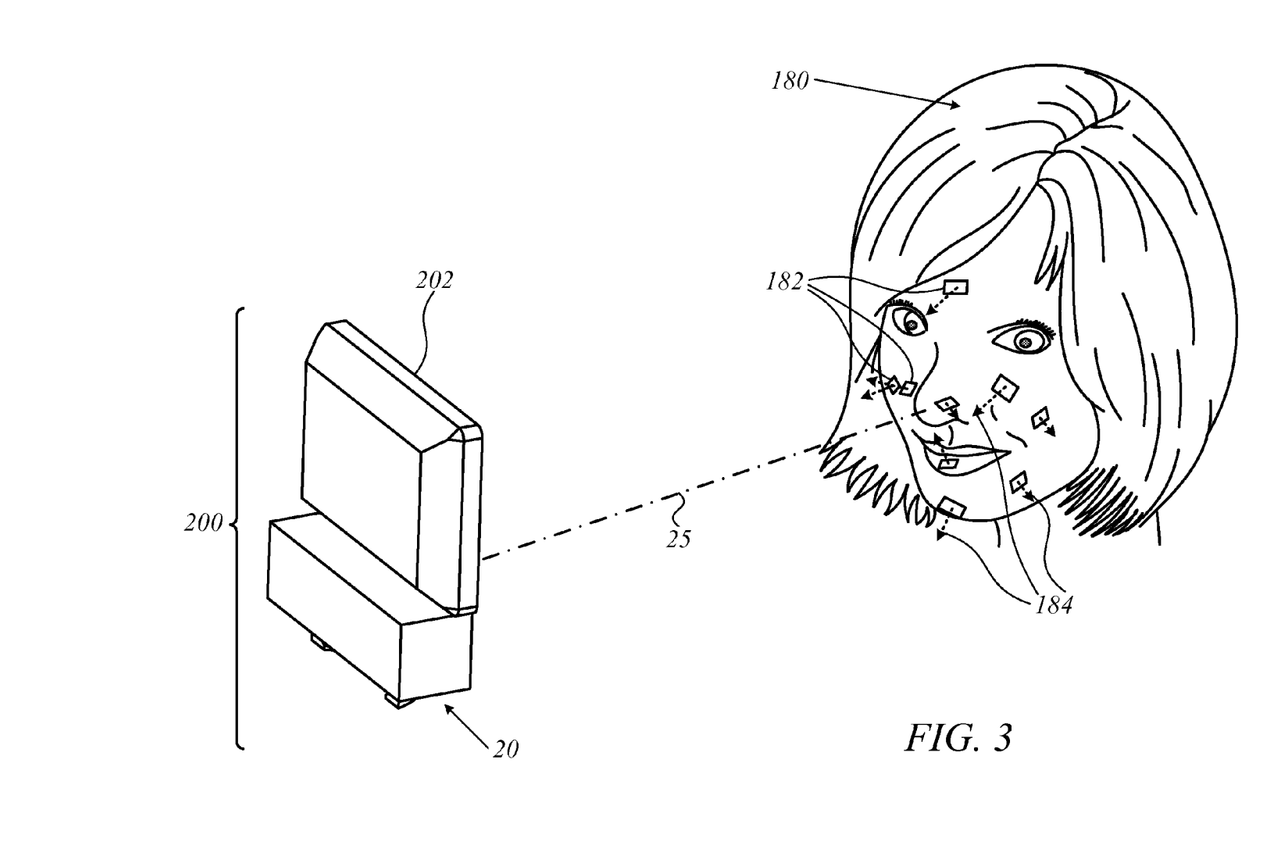
FIG. 3 schematically shows a human computer interface comprising a range camera operating to determine reflectance of a user's facial skin in accordance with an embodiment of the disclosure.

For example, FIG. 2B schematically shows a scenario for which calibration surface 50 is perpendicular to optic axis 25 and therefore $\hat{\eta}(i,j,Z_o)$ is parallel to the optic axis, but a scene region $A_T(X_i,Y_j,Z_k)$ is tilted relative to scene region $A(X_i,Y_j,Z_k)$ shown in FIGS. 2A and 2B. Whereas the normal $\hat{\eta}(i,j,Z_o)$ to scene region $A(X_i,Y_j,Z_k)$ is parallel to optic axis 25, tilted scene region $A_T(X_i,Y_j,Z_k)$ has a normal $\hat{\eta}(i,j,Z_k,T)$ that is tilted with respect to optic axis 25 by optionally an angle β. As a result of the tilt, $A_T(X_i,Y_j,Z_k)$ has an area $A_T(i,j,Z_k)$ imaged on photosensor pixel p(i,j,k) equal to $$A_T(i,j,Z_k) = [A_P(Z_k/f)^2][\cos\theta(i,j,Z_k)/\hat{R}(i,j,Z_k) \cdot \hat{\eta}(i,j,Z_k,T)] \quad (23)$$
$$= A(i,j,Z_k)[\cos\theta(i,j,Z_k)/\hat{R}(i,j,Z_k) \cdot \hat{\eta}(i,j,Z_k,T)],$$

where $[A_p(Z_k/f)^2]$ is the area $A(i,j,Z_k)$ of non-tilted scene region $A(X_i,Y_j,Z_k)$ determined similarly to determining $\mathcal{A}(i,j,Z_o)$ in accordance with equation (1).

In addition, in an equation for total irradiance $TIR(A_T(X_i,Y_j,Z_k))$ of tilted scene region $A_T(X_i,Y_j,Z_k)$ similar to equation (2) for $TIR(\mathcal{A}(X_i,Y_j,Z_o))$, it may not be appropriate, as provided for $TIR(\mathcal{A}(X_i,Y_j,Z_o))$ by equation (3), to replace $\hat{\eta}(i,j,Z_k,T) \cdot P_o(\theta',\varphi',(i,j,Z_k))$ with $P_o(\theta',\varphi',(i,j,Z_k))[Z_k/R'(i,j,Z_k)]$. In equation (3), $\hat{\eta}(i,j,Z_o) \cdot P_o(\theta',\varphi',(i,j,Z_o))$ is replaced by $P_o(\theta',\varphi',(i,j,Z_o))[Z_o/R'(i,j,Z_o)]$ under the assumption that normal $\hat{\eta}(i,j,Z_o)$ to $\mathcal{A}(X_i,Y_j,Z_o)$ is parallel to optic axis 25 and as a result $\hat{\eta}(i,j,Z_o) \cdot P_o(\theta',\varphi',(i,j,Z_o)) = \cos\theta'(i,j,Z_o) = [Z_o/R'(i,j,Z_o)]$. Irradiance $RSI(i,j,Z_k)$ of $A(X_i,Y_j,Z_k)$ given by expression (11) is similarly dependent on the assumption that normal $\hat{\eta}(i,j,Z_k)$ to $A(X_i,Y_j,Z_k)$ is parallel to optic axis 25 and therefore that $\hat{\eta}(i,j,Z_k) \cdot P_o(\theta',\varphi',(i,j,Z_k)) = \cos\theta'(i,j,Z_k) = [Z_k/R'(i,j,Z_k)]$.

Since the assumption that $\hat{\eta}(i,j,Z_k)$ is parallel to optic axis 25 and its consequence that $\cos\theta'(i,j,Z_o) = [Z_o/R'(i,j,Z_o)]$ do not obtain for $\hat{\eta}(i,j,Z_k,T)$, equation (17) may not provide a satisfactory value for ρ(i,j,k) for tilted scene region $A_T(X_i,Y_j,Z_k)$.

Therefore, in an embodiment of the disclosure, for a tilted scene region such as $A_T(X_i,Y_j,Z_k)$ equation (17) may be adjusted for tilt by multiplying the right hand side of the equation by a "tilt factor" (TF) defined by an expression:

$$TF = [Z_k/R'(i,j,Z_k)\cos\theta(i,j,Z_k)][\hat{R}(i,j,Z_k) \cdot \hat{\eta}(i,j,k,T)/\hat{R}'(i,j,Z_k) \cdot \hat{\eta}(i,j,k,T)]. \quad (24)$$

And if reflectance for a tilted scene region is represented by $\rho_T(i,j,k)$, then $\rho_T(i,j,k) = TF\rho(i,j,k)$, which if ρ(i,j,k) is determined in accordance with equation (17), equals $$TF\rho_o(Z_o/Z_k)^4[RSI(i,j,Z_k)/RCI(i^*,j^*,Z_o)][(R(i,j,Z_k)/R(i^*,j^*,Z_o))(R'(i,j,Z_k)/R'(i^*,*j,Z_o))]^3. \quad (25)$$

The expression for TF assumes that registered calibration irradiance $RCI(i,j,Z_o)$ is determined for a planar calibration surface 50 as shown in FIG. 1 and defined by equation (10), and adjusts equation (17) or (22) to account for a difference in direction between $\hat{\eta}(i,j,Z_o)$ and $\hat{\eta}(i,j,k,T)$ in determining total irradiance of $A_T(i,j,Z_k)$ by light from light source 42. In particular it is noted that total irradiance $TIR(A(X_i,Y_j,Z_k))$ of a scene region $A(X_i,Y_j,Z_k)$ having normal parallel to optic axis 25 may be written, similarly to equations (2) and (5):

$$TIR(A(X_i,Y_j,Z_k)) = A(i,j,Z_o)\hat{\eta}(i,j,Z_k) \cdot \quad (26)$$
$$P_o(\theta',\varphi',(i,j,Z_k))/R'(i,j,Z_k)^2$$
$$= (A_P/f^2)P_o(\theta',\varphi',(i,j,Z_k))[Z_k/R'(i,j,Z_k)^3].$$

Total irradiance of tilted scene region $A_T(X_i,Y_j,Z_k)$ by light from light source 42 may similarly be written, $$TIR(A_T(X_i,Y_j,Z_k)) = A_T(i,j,Z_k)\hat{\eta}(i,j,Z_k,T) \cdot \quad (27)$$
$$P_o(\theta',\varphi',(i,j,Z_k))/R'(i,j,Z_k)^2$$
$$= A_T(i,j,Z_k)P_o(\theta',\varphi',(i,j,Z_k))$$

-continued $$(\hat{\eta}(i,j,Z_k,T) \cdot \hat{R}'(i,j,Z_k))/R'(i,j,Z_k)^2$$

$$= A_T(i,j,Z_k)P_o(\theta', \varphi', (i,j,Z_k))$$

$$(\hat{\eta}(i,j,Z_k,T) \cdot \hat{R}'(i,j,Z_k))$$

$$(R'(i,j,Z_k)/Z_k)[Z_k/R'(i,j,Z_k)^3].$$

Using expression (23) for $A_T(i,j,Z_k)$ in equation (27) results in:

$$TIR(A_T(X_i,Y_j,Z_k)) = [\cos\theta(i,j,Z_k)/\hat{R}(i,j,Z_k) \cdot \hat{\eta}(i,j,Z_k,T)] \cdot \quad (28)$$

$$(\hat{\eta}(i,j,Z_k,T) \cdot R'(i,j,Z_k))(R'(i,j,Z_k)/Z_k) \times$$

$$[A_p(Z_k/f)^2]P_o(\theta',\varphi',(i,j,Z_k))$$

$$[Z_k/R'(i,j,Z_k)^3]$$

$$= [\cos\theta(i,j,Z_k)/\hat{R}(i,j,Z_k) \cdot \hat{\eta}(i,j,Z_k,T)]$$

$$(\hat{\eta}(i,j,Z_k,T) \cdot R'(i,j,Z_k)/Z_k) \times$$

$$TIR(A(X_i,Y_j,Z_k))$$

$$= \cos\theta(i,j,Z_k)(R'(i,j,Z_k)/Z_k)[(\hat{\eta}(i,j,Z_k),T) \cdot$$

$$R'(i,j,Z_k))/(\hat{R}(i,j,Z_k) \cdot \hat{\eta}(i,j,Z_k,T)] \times$$

$$TIR(A(X_i,Y_j,Z_k))$$

$$= TF^{-1}TIR(A(X_i,Y_j,Z_k)).$$

Expression (28) defines TF for planar calibration surface 50 and a tilted scene region $TIR(A_T(X_i,Y_j,Z_k))$.

Equations (23)-(28) express variables and reflectance of a tilted surface region $A_T(i,j,Z_k)$ of a scene imaged by range camera 20 as a function of a unit normal, $\hat{\eta}(i,j,Z_k,T)$ of the region, which is not necessarily parallel to optic axis 25. In an embodiment of the disclosure, range camera 20 acquires 3D spatial coordinates, $X_i$, $Y_j$, and $Z_k$, for points in a scene that define a range image of the scene and thereby 3D surfaces for features in the scene. In an embodiment of the disclosure, range camera 20 processes the 3D spatial coordinates to determine gradients for regions of the surfaces and therefrom normals $\hat{\eta}(i,j,Z_k,T)$ to the surface regions. The normals are optionally used in accordance with equations (23)-(28) or equations similar to equations (23)-(28) to determine reflectances for the surface regions. It is noted that whereas equations (23)-(28) relax a constraint that $\hat{\eta}(i,j,Z_k,T)$ is parallel to optic axis 50, the equations are constrained by an assumption that intensity of reflected light per unit solid angle from an illuminated surface is independent of angle of reflection relative to normals $\hat{\eta}(i,j,Z_k)$ and $\hat{\eta}(i,j,Z_k,T)$. In an embodiment of the disclosure the constraint may be relaxed to determine $RCI(i,j,Z_o)$ and it may be assumed for example that intensity of reflected light decreases proportional to the cosine of an angle that direction of propagation of the reflected light makes relative to normal $\hat{\eta}(i,j,Z_k)$ and/or normal $\hat{\eta}(i,j,Z_k,T)$ FIG. 3 schematically shows a user 180 interacting with a human computer interface (HCI) 200 optionally comprising a video screen 202 for providing visual information to the user and a range camera 20 having an optic axis 25 (FIG. 1). Range camera 20 images the user and user gestures to communicate information from the user to a computer (not shown), and operates in accordance with an embodiment of the disclosure to determine reflectance of regions of the facial skin of user 180 to characterize the user and user gestures. Controller 28 of camera 20 optionally comprises a calibration image having RCIs for pixels 23 in photosensor 22 determined in accordance with an embodiment of the disclosure. Optionally, the RCIs are determined as described with reference to FIG. 1. Controller 28 controls range camera 20 to acquire range images and picture images of user 180 and, optionally, determines skin reflectance for facial skin regions of user 180 responsive to the range and picture images of the user, and RCIs comprised in the calibration image.

Controller 28 may determine skin reflectance for regions of facial skin of user 180 in accordance with equation (17) or equation (22) under the assumption that normals to regions of the user's facial skin are substantially parallel to optic axis 25 of the range camera. Controller 28 may determine skin reflectance for regions of facial skin of user 180 in accordance with equations (23-28) after determining normals $\hat{\eta}(i,j,Z_k,T)$ to the user's facial skin regions. Optionally, the normals are determined by calculating gradients to surfaces of the user's facial skin responsive to 3D spatial coordinates provided by the range images. FIG. 3 schematically shows facial skin regions, represented by small rectangles 182 of user 180 and normals $\hat{\eta}(i,j,Z_k,T)$ schematically represented by arrows 184 to the facial skin regions.

In an embodiment of the disclosure range camera 20 illuminates the face of user 180 with IR light and monitors changes in IR reflectance of the user's facial skin region to determine the user's heartbeat and/or temperature. Optionally controller 28 uses changes in reflectance to provide information characterizing the user's emotional state. For example to determine if the user is blushing or angry.

There is therefore provided in accordance with an embodiment of the disclosure a range camera operable to determine distances to and reflectance for features of a scene that the range camera images, the range camera comprising: a light source operable to transmit light to illuminate a scene that the range camera images; a photosensor having light sensitive pixels; optics having an optical axis and optical center configured to receive light reflected from the transmitted light by features in the scene and image the reflected light on a plurality of the pixels, each of which plurality of pixels registers reflected light from a feature of the scene that the optics images on the pixel to provide a registered scene irradiance (RSI) for the feature; a calibration image comprising a registered calibration irradiance (RCI) for each of the light sensitive pixels that provides a measure of irradiance that the pixel registers responsive to light reflected from light transmitted by the light source by a region of a calibration surface having known shape, reflectance, and location that the range camera images on the pixel; and a controller operable to determine a reflectance for a feature of the scene imaged on a first pixel of the photosensor comprised in the plurality of pixels responsive to the RSI for the feature and an RCI for a region of the calibration surface imaged on a second pixel of the photosensor corresponding to the feature imaged on the first pixel.

In an embodiment, the feature imaged on the first pixel and the corresponding region of the calibration surface imaged on the second pixel are imaged on their respective pixels with light they reflect from light transmitted along a same direction by the light source. The determined reflectance for the feature imaged on the first pixel may be a function of a ratio RSI/RCI times reflectance $\rho_o$ of the corresponding region of the calibration surface.

In an embodiment, the range camera determines a distance vector R for the feature that defines a location of the feature in a field of view (FOV) of the camera relative to the optics and a distance vector R' that defines a location for the feature imaged on the first pixel in the FOV relative to the light source and uses R and R' to determine a location on the calibration surface of the corresponding region of the calibration surface. Optionally, the range camera determines a distance vector $R_o$ for the corresponding region of the calibration surface in the FOV of the range camera relative to the optics, and a distance vector $R_o'$ that defines a location of the corresponding region in the FOV relative to a location of the light source responsive to the determined location of the corresponding region of the calibration surface.

In an embodiment, the reflectance for the feature imaged on the first pixel is proportional to $\rho_o(RSI/RCI)[(|R|/|R_o|)(|R'|/|R_o'|)]^3$ where $\rho_o$ is reflectance of the corresponding region of the calibration surface.

Optionally, the calibration surface is oriented perpendicular to an optical axis of the camera at a fixed distance $Z_o$ from the optical center along the optical axis and the feature imaged on the first pixel is located at a distance Z from the optical center along the optical axis.

In an embodiment, the reflectance for the feature imaged on the first pixel is proportional to $\rho_o(Z_o/Z)^4(RSI/RCI)[(|R|/|R_o|)(|R'|/|R_o'|)]^3$ where $\rho_o$ is reflectance of the corresponding region of the calibration surface.

In an embodiment of the disclosure, the controller is operable to determine a tilt factor TF for the feature imaged on the first pixel and use the tilt factor to determine the reflectance for the feature, wherein $TF=[Z/(|R'|(\hat{R}\cdot\hat{Z}))][(\hat{R}\cdot\hat{\eta})/(\hat{R}'\cdot\hat{\eta})]$ and $\hat{\eta}$ is a unit normal to a surface of the feature imaged on the first pixel, "Z" is distance of the feature from the optical center along the optical axis, and $\hat{R}$ and $\hat{R}'$ are unit vectors pointing from the feature to the optical center and the light source respectively. Optionally, the reflectance for the feature imaged on the first pixel is proportional to $TF\rho_o(Z_o/Z)^4(RSI/RCI)[(|R|/|R_o|)(|R'|/|R_o'|)]^3$ where $\rho_o$ is a known reflectance of the region imaged on the second pixel. The controller may control the range camera to acquire a range image of the scene and determines $\hat{\eta}$ responsive to a gradient of a surface of the feature defined by the range image.

In an embodiment of the disclosure, the reflectance of the calibration surface is substantially the same for all regions of the calibration surface having an RCI comprised in the calibration image. In an embodiment of the disclosure, the calibration surface is planar.

There is further provided in accordance with an embodiment of the disclosure a method of determining reflectance for a feature of a scene, the method comprising: using an active lighting range camera to acquire a range image and a picture image of the scene responsive to light transmitted by the range camera to illuminate the scene that is reflected by features in the scene back to the range camera; determining a location of the feature in the FOV responsive to the range image; determining registered irradiance of the range camera by light reflected from the transmitted light by the feature responsive to the picture image; determining a corresponding region of a calibration surface imaged in a calibration image acquired by the range camera; determining registered irradiance of the range camera by light reflected from the transmitted light by the corresponding region responsive to the calibration image; and using the determined registered irradiances from the feature and the corresponding calibration region and known reflectance of the calibration surface to determine the reflectance of the feature.

Optionally, determining the corresponding region of the calibration surface comprises determining a region of the calibration surface for which light from the range camera that illuminates the region to acquire the calibration image is transmitted along a same direction that the range camera illuminates the feature to acquire the picture image. Determining the reflectance of the feature may comprise multiplying the known reflectance by a ratio equal to the registered irradiance from the feature divided by the registered irradiance from the corresponding region.

The method may comprise determining a unit normal $\hat{\eta}$ to a surface of the feature responsive to the range image and using the unit normal to determine the reflectance. Optionally, using the normal comprises determining a first distance vector from an optical center of the range camera to the feature responsive to the range image and determining a first scalar product of the normal with the first distance vector. Using the normal may comprise determining a second distance vector from a location from which the range camera transmits light to illuminate the scene to the feature responsive to the range image and determining a second scalar product of the normal with the second distance vector. Optionally, determining the reflectance comprises determining a ratio between the first scalar product and the second scalar product.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments. Some embodiments utilize only some of the features or possible combinations of the features. Variations of embodiments of the disclosure that are described, and embodiments comprising different combinations of features noted in the described embodiments, will occur to persons of the art. The scope of the invention is limited only by the claims.

The invention claimed is:

1. A range camera operable to determine distances to and reflectance for features of a scene that the range camera images, the range camera comprising:
   a light source operable to transmit light to illuminate a scene that the range camera images;
   a photosensor having a plurality of light sensitive pixels;
   optics having an optical axis and optical center configured to receive light reflected from the transmitted light by features in the scene and image the reflected light on the plurality of pixels, each of which pixel of the plurality of pixels registers reflected light from a feature of the scene that the optics images on the pixel to provide a registered scene irradiance (RSI) for the feature;
   a calibration image comprising a registered calibration irradiance (RCI) for each of the plurality of light sensitive pixels that provides a measure of irradiance that the pixel registers responsive to light reflected from light transmitted by the light source by a region of a calibration surface having known shape, reflectance, and location that the range camera images on the pixel; and
   a controller operable to determine a reflectance for a feature of the scene imaged on a first pixel of the plurality of pixels responsive to the RSI for the feature and an RCI for a region of the calibration surface imaged on a second pixel of the plurality of pixels corresponding to the feature imaged on the first pixel.

2. The range camera according to claim 1 wherein the feature imaged on the first pixel and the corresponding region of the calibration surface imaged on the second pixel are imaged on their respective pixels with light they reflect from light transmitted along a same direction by the light source.

3. The range camera according to claim 1 wherein the determined reflectance for the feature imaged on the first pixel is a function of a ratio RSI/RCI times reflectance $\rho_o$ of the corresponding region of the calibration surface.

4. The range camera according to claim 1 wherein the range camera determines a distance vector R for the feature that defines a location of the feature in a field of view (FOV) of the camera relative to the optics and a distance vector R' that defines a location for the feature imaged on the first pixel in the FOV relative to the light source and uses R and R' to determine a location on the calibration surface of the corresponding region of the calibration surface.

5. The range camera according to claim 4 wherein the range camera determines a distance vector $R_o$ for the corresponding region of the calibration surface in the FOV of the range camera relative to the optics, and a distance vector $R_o'$ that defines a location of the corresponding region in the FOV relative to a location of the light source responsive to the determined location of the corresponding region of the calibration surface.

6. The range camera according to claim 5 wherein the reflectance for the feature imaged on the first pixel is proportional to $\rho_o(RSI/RCI)[(|R|/|R_o|)(|R'|/|R_o'|)]^3$ where $\rho_o$ is reflectance of the corresponding region of the calibration surface.

7. The range camera according to claim 6 wherein the calibration surface is oriented perpendicular to an optical axis of the camera at a fixed distance $Z_o$ from the optical center along the optical axis and the feature imaged on the first pixel is located at a distance Z from the optical center along the optical axis.

8. The range camera according to claim 7 wherein the reflectance for the feature imaged on the first pixel is proportional to $\rho_o(Z_o/Z)^4(RSI/RCI)[(|R|/|R_o|)(|R'|/|R_o'|)]^3$ where $\rho_o$ is reflectance of the corresponding region of the calibration surface.

9. The range camera according to claim 1 wherein the controller is operable to determine a tilt factor TF for the feature imaged on the first pixel and use the tilt factor to determine the reflectance for the feature, wherein $TF=[Z/(|R'|(\hat{R}\cdot\hat{Z}))][(\hat{R}\cdot\hat{\eta})/(\hat{R}'\cdot\hat{\eta})]$ and $\hat{\eta}$ is a unit normal to a surface of the feature imaged on the first pixel, "Z" is distance of the feature from the optical center along the optical axis, and $\hat{R}$ and $\hat{R}'$ are unit vectors pointing from the feature to the optical center and the light source respectively.

10. The range camera according to claim 9 wherein the reflectance for the feature imaged on the first pixel is proportional to $TF\rho_o(Z_o/Z)^4(RSI/RCI)[(|R|/|R_o|)(|R'|/|R_o'|)]^3$ where $\rho_o$ is a known reflectance of the region imaged on the second pixel.

11. The range camera according to claim 9 wherein the controller controls the range camera to acquire a range image of the scene and determines $\hat{\eta}$ responsive to a gradient of a surface of the feature defined by the range image.

12. The range camera according to claim 1 wherein the reflectance of the calibration surface is substantially the same for all regions of the calibration surface having an RCI comprised in the calibration image.

13. The range camera according to claim 1 wherein the calibration surface is planar.

14. A method of determining reflectance for a feature of a scene, the method comprising:
using an active lighting range camera to acquire a range image and a picture image of the scene responsive to light transmitted by the range camera to illuminate the scene that is reflected by features in the scene back to the range camera;
determining a location of the feature in the FOV responsive to the range image;
determining registered irradiance of the range camera for light reflected from the transmitted light by the feature responsive to the picture image;
determining a corresponding region of a calibration surface imaged in a calibration image acquired by the range camera;
determining registered irradiance of the range camera for light reflected from the transmitted light by the corresponding region responsive to the calibration image; and
using the determined registered irradiances from the feature and the corresponding calibration region and known reflectance of the calibration surface to determine the reflectance of the feature.

15. The method according to claim 14 wherein determining the corresponding region of the calibration surface comprises determining a region of the calibration surface for which light from the range camera that illuminates the region to acquire the calibration image is transmitted along a same direction that the range camera illuminates the feature to acquire the picture image.

16. The method according to claim 14 wherein determining the reflectance of the feature comprises multiplying the known reflectance by a ratio equal to the registered irradiance from the feature divided by the registered irradiance from the corresponding region.

17. The method according to claim 16 and comprising determining a unit normal $\hat{\eta}$ to a surface of the feature responsive to the range image and using the unit normal to determine the reflectance.

18. The method according to claim 17 wherein using the normal comprises determining a first distance vector from an optical center of the range camera to the feature responsive to the range image and determining a first scalar product of the normal with the first distance vector.

19. The method according to claim 18 wherein using the normal comprises determining a second distance vector from a location from which the range camera transmits light to illuminate the scene to the feature responsive to the range image and determining a second scalar product of the normal with the second distance vector.

20. The method according to claim 19 wherein determining the reflectance comprises determining a ratio between the first scalar product and the second scalar product.

21. A range camera operable to determine distances to and reflectance for features of a scene that the range camera images, the range camera comprising:
a light source operable to transmit light to illuminate a scene that the range camera images;
a photosensor having a plurality of light sensitive pixels;
a look up table (LUT) having for each pixel of the plurality of light sensitive pixels a set of values for a first feature having known reflectance that is imaged on the pixel from a known first distance from the camera and illuminated by light at known intensity from the light source, the set of values comprising a registered calibration irradiance (RCI) for light reflected by the first feature from the illuminating light; and a controller that, determines a reflectance of a second feature imaged on the pixel from a second distance responsive to a square of the ratio of the first distance divided by the second distance, the RCI, and a registered scene irradiance (RSI) that the pixel provides for light from the light source that is reflected by the second feature and imaged on the pixel.

22. The range camera according to claim 21 wherein the LUT comprises at least one coefficient of a power series that provides an expected registered irradiance that the pixel generates for light from the light source reflected by the first feature for a displacement of the first feature from the first distance.

23. The range camera according to claim 22 wherein the controller determines the reflectance responsive to a coefficient of the at least one coefficient.

* * * * *